United States Patent
Inoue et al.

(10) Patent No.: US 7,850,840 B2
(45) Date of Patent: Dec. 14, 2010

(54) METHOD OF DIAGNOSING MALFUNCTION IN GAS CONCENTRATION DETECTING UNIT AND MALFUNCTION DIAGNOSTIC APPARATUS THEREOF

(75) Inventors: Yoshinori Inoue, Nagoya (JP); Norikazu Ieda, Nagoya (JP); Masahiro Tanaka, Nagoya (JP); Reina Fukagai, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 316 days.

(21) Appl. No.: 11/884,262

(22) PCT Filed: Feb. 16, 2006

(86) PCT No.: PCT/JP2006/302696

§ 371 (c)(1),
(2), (4) Date: Aug. 14, 2007

(87) PCT Pub. No.: WO2006/088073

PCT Pub. Date: Aug. 24, 2006

(65) Prior Publication Data

US 2008/0060939 A1    Mar. 13, 2008

(30) Foreign Application Priority Data

Feb. 16, 2005    (JP) .............................. 2005-038526

(51) Int. Cl.
   *G01N 27/41*    (2006.01)
(52) U.S. Cl. .................. 205/784; 204/401; 204/425
(58) Field of Classification Search .............. 204/401, 204/425, 426; 205/781, 784; 73/23.31, 23.32
   See application file for complete search history.

(56) References Cited

U.S. PATENT DOCUMENTS

| 5,392,643 | A | 2/1995 | O'Kennedy et al. |
| 6,136,169 | A | 10/2000 | Okamoto |
| 7,142,976 | B2 | 11/2006 | Inoue et al. |

(Continued)

FOREIGN PATENT DOCUMENTS

JP    11-107830    4/1999

(Continued)

*Primary Examiner*—Kaj K Olsen
(74) *Attorney, Agent, or Firm*—Sughrue Mion, PLLC

(57) ABSTRACT

To provide a malfunction diagnosing method and apparatus capable of reliably determining a malfunction even where the malfunction occurs in a common wire connecting a gas sensor and a control circuit for driving it. In a gas concentration measurement unit 1 having a sensor control circuit 50 which is connected to a sensor element 10 including an oxygen pump cell 14 and an oxygen concentration detection cell 24 and controls and drives this sensor element 10, a variation state of a terminal voltage at one connecting point (specifically, a Vs+ terminal) other than connecting points between electrodes facing a measurement chamber of each cell 14 and 24 and a common wire 24 is detected by a malfunction detection circuit 53 and an arithmetic processor 54. Based on this variation state of the terminal voltage, diagnosis of malfunction in the common wire 42 is executed. When the common wire 42 is broken, the terminal voltage at the Vs+ terminal varies with oscillations. Therefore, the malfunction detection circuit 53 and the arithmetic processor 54 detect this voltage variation with oscillations to output a malfunction determination signal to a CPU.

12 Claims, 4 Drawing Sheets

U.S. PATENT DOCUMENTS

2004/0217001 A1 11/2004 Hada et al.
2004/0222094 A1 11/2004 Ieda et al.
2004/0238378 A1* 12/2004 Kumazawa et al. ......... 205/781
2006/0157348 A1 7/2006 Inoue et al.

FOREIGN PATENT DOCUMENTS

| | | |
|---|---|---|
| JP | 2003-97342 A | 4/2003 |
| JP | 2004-301832 A | 10/2004 |
| JP | 2004-317488 A | 11/2004 |
| JP | 2006-47278 | 2/2006 |
| JP | 2006-208363 | 8/2006 |

* cited by examiner

METHOD OF DIAGNOSING MALFUNCTION IN GAS CONCENTRATION DETECTING UNIT AND MALFUNCTION DIAGNOSTIC APPARATUS THEREOF

CROSS-REFERENCE TO RELATED APPLICATIONS

This application is a 371 of PCT/JP2006/302696 filed on Feb. 16, 2006 and claims priority form Japanese Patent Application No. 2005-038526 filed Feb. 16, 2005.

TECHNICAL FIELD

The present invention relates to a method of diagnosing a malfunction in a gas concentration detecting unit, which is applied to air-fuel ratio feedback control of an internal combustion engine, and a malfunction diagnostic apparatus for the gas concentration detecting unit.

BACKGROUND ART

In an internal combustion engine such as a gasoline engine, air-fuel ratio feedback control for detecting the concentration of a specific gas in exhaust gas by a gas sensor mounted to an exhaust pipe and controlling a mixture ratio of fuel and air, based on the result of its detection is now being conducted to reduce CO, NOx and HC in the exhaust gas.

As the gas sensor for realizing such air-fuel ratio control, there has been known a full-region air-fuel ratio sensor (hereinafter also called simply "UEGO sensor") wherein two cells (specifically, an oxygen pump cell and an oxygen concentration detection cell) equipped with electrodes on both surfaces of a solid electrolytic layer formed principally of zirconia are laminated with a hollow measurement chamber interposed therebetween, and exhaust gas is introduced into the measurement chamber via a diffusion resistance body to detect an oxygen concentration in the exhaust gas.

The electrodes of the respective cells that constitute the UEGO sensor are electrically connected to a controller for driving and controlling the sensor. The controller executes a process for allowing current to flow through the oxygen pump cell so that a voltage outputted from the oxygen concentration detection cell will be a pre-set value, thereby to control the oxygen concentration in the measurement chamber to a constant value and measuring an oxygen concentration (i.e., air-fuel ratio) in the exhaust gas from the value of the current flowing through the oxygen pump cell. Incidentally, the UEGO sensor is provided with one common wire (common harness) for commonly connecting the respective electrodes of the cells, facing the measurement chamber in order to supply a common reference potential to the respective cells that constitute the sensor.

Meanwhile, since no reference potential is supplied to the respective cells where the common wire is broken, the controller does not normally perform feedback control for making constant the oxygen concentration of the measurement chamber and hence the UEGO sensor is not able to measure the oxygen concentration.

Therefore, as an air-fuel ratio system having this type of gas sensor, there has been known one which diagnoses the presence or absence of a malfunction in common wire (refer to, for example, Patent Document 1).

The air-fuel ratio system disclosed in Patent Document 1 determines whether, in diagnosing a break in a common wire (COM terminal), potentials corresponding to terminal voltages at three connecting points (including connecting points to which the common wire is connected) for connecting respective sensor cells and a sensor control circuit fall within a predetermined range. Then, information about such a result of determination is superimposed on output signals at three output terminals (specifically, a VRPVS terminal, a VIP terminal, and a VVS terminal), and the break in the common wire is diagnosed based on the combination of the three output signals.

[Patent Document 1] Jpn. unexamined patent publication No. 2003-97432

DISCLOSURE OF THE INVENTION

Problems that the Invention is to Solve

In Patent Document 1, however, the output signals from the three output terminals are necessary to diagnose the break in the common wire, and a detecting method was prone to increase in complexity.

There is also a case in which even when the break occurs in the common wire, the combination of the three output signals is not necessarily brought to a combination set in advance. There was a fear of the occurrence of an error in a diagnostic result.

The present invention has been made in view of such problems. It is therefore an object of the present invention to make it possible to reliably determine a malfunction (specifically, break) in common wire even where the malfunction or trouble occurs in the common wire for connecting a gas sensor including an oxygen pump cell and an oxygen concentration detection cell and a control circuit for driving and controlling the gas sensor.

Means for Solving the Problem

Now, the present inventors have focused attention on the point that when a malfunction (specifically break or disconnection) has occurred in a common wire commonly connected to respective electrodes of cells on the side facing a measurement chamber, input/output signals of the respective cells produce voltage variations different from those at the normal condition, so that feedback control for making constant an oxygen concentration of the measurement chamber is not normally performed.

Here, to achieve the above object, in a first aspect (1) the present invention provides a method for diagnosing a malfunction of a gas concentration detecting unit comprising: a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein, and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the method comprising the step of: diagnosing a malfunction of the common wire on the basis of a state of variations in terminal voltage at any other than a connecting point of the common wire, of connecting points for connecting the control circuit and the respective electrodes of the cells.

When the malfunction occurs in the common wire as described above, the input/output signals of the respective cells produce the voltage variations different from those at the normal condition. When the input/output signals of the respective cells produce such voltage variations, associated voltage variations occur in the voltage (terminal voltage) at any other than the connecting point of the common wire, of the connecting points for connecting the control circuit and the respective electrodes of the cells. Thus, in the present invention, the capturing of the state of the variations in terminal voltage at any other than s connecting point to which the common wire is connected is specified.

Thus, the malfunction diagnosing method for the gas concentration detecting unit of the present invention is capable of carrying out a diagnosis of a malfunction in common wire simply and with satisfactory accuracy by simply detecting the state of the variations in terminal voltage at the connecting point other than the connecting point of the common wire. Further, the voltage variations produced upon the malfunction in the common wire cause relatively large variations. Therefore, the capturing of the state of the variations in terminal voltage at any other than the connecting point of the common wire makes it easy to distinguish between the time when the common wire is abnormal and the time when it is normal and makes it possible to reliably carry out the malfunction diagnosis of the common wire.

Incidentally, "any point other than connecting point of the common wire, of the connecting points for connecting the control circuit and the respective electrodes of the cells" may be a connecting point between the electrode and the control circuit, the electrode being located on the opposite side of the electrode lying on the side facing the measurement chamber, of the oxygen concentration detection cell, or may be a connecting point between the electrode and the control circuit, the electrode being located on the opposite side of the electrode lying on the side facing the measurement chamber, of the oxygen pump cell.

Further, as a concrete aspect of the above malfunction diagnosing method, preferably, as set forth in a preferred embodiment (2) the presence or absence of occurrence of a malfunction in the common wire is determined based on the presence or absence of oscillations in the terminal voltage.

Since the input/output signal of each cell is apt to produce an oscillation state when the malfunction occurs in the common wire, variations in voltage with oscillations occur in the voltage (terminal voltage) at the connecting point other than the connecting points to which the common wire is connected. Therefore, the presence or absence of the occurrence of the malfunction is specifically determined based on the presence or absence of the oscillations thereby to make it possible to carry out a malfunction diagnosis with satisfactory accuracy.

In order to measure the state of the variations in terminal voltage at any other than the connecting points to which the common wire is connected, and its oscillated state and carry out a malfunction diagnosis, the frequency of the terminal voltage is measured and the presence or absence of a malfunction may be determined or judged based on the measured frequency. As defined in yet another preferred embodiment (3), however, preferably, a detected count is accumulated one by one when the terminal voltage exceeds a preset threshold value and subsequently falls below the threshold value. Alternatively, preferably, a detected count is accumulated one by one when the terminal voltage falls below the threshold value and subsequently exceeds the same, and the occurrence of the malfunction is determined when the accumulated number of detect counts has reached a predetermined value within a predetermined time interval.

If done in this way, then the state of the variations in terminal voltage and its oscillated state can be grasped simpler even though a complex process such as an analysis of the frequency of the terminal voltage at any connecting point other than the connecting point to which the common wire is connected is not executed. By extension, a simple and accurate malfunction diagnosis of the common wire can be carried out.

Incidentally, the present invention is not limited to a voltage value used as is, as the terminal voltage to be compared with the threshold value. A value obtained by dividing the terminal voltage using a divider circuit may be used. Alternatively, a voltage value obtained by amplifying the terminal voltage at a predetermined amplification factor may be used.

In order to measure a state of variations in terminal voltage at any connecting point other than the connecting points to which the common wire is connected, and carry out a malfunction diagnosis, as defined in yet another preferred embodiment (4), preferably, a detected count is accumulated one by one when the terminal voltage exceeds a preset first threshold value and subsequently falls below a second threshold value larger than the first threshold value, or a detected count is accumulated one by one when the terminal voltage falls below the second threshold value and subsequently exceeds the first threshold value, and it is determined that a malfunction has occurred when the accumulated number of the detected counts has reached a predetermined value within a predetermined time.

Thus, even when the malfunction diagnosis is performed, the state of the variations in the terminal voltage and its oscillated state can be captured simply. By extension, a simple and accurate malfunction diagnosis of the common wire can be carried out. Further, the malfunction diagnosing method for the gas concentration detecting unit of the present invention makes use of two different values without setting the number of threshold values for grasping or capturing the state of the variations in terminal voltage to one. Thus, even when the terminal voltage frequently fluctuates with respect to either of the threshold values due to an influence such as noise, it is not recognized as being a voltage variation and a misjudgment made as to the occurrence of the malfunction in common wire due to the influence of noise is prevented. Further, a malfunction diagnosis of the common wire, which is excellent in noise resistance and more satisfactory in accuracy, can be carried out.

Incidentally, the present invention is not limited to a voltage value used as is, as the terminal voltage to be compared with each of the first and second threshold values. A value obtained by dividing the terminal voltage using a divider circuit may be used. Alternatively, a voltage value obtained by amplifying the terminal voltage at a predetermined amplification factor may be used.

Further, to achieve the above object, in a second aspect (5) the present invention provides a malfunction diagnostic apparatus for a gas concentration detecting unit comprising: a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein; and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the malfunction diagnostic apparatus comprising: malfunction diagnosing means for diagnosing a malfunction of the common wire on the basis of a state of variations in terminal voltage at any other than a connecting point of the common wire, of connecting points for connecting the control circuit and the respective electrodes of the cells.

According to the malfunction diagnostic apparatus for the gas concentration detecting unit, which has been constructed in this way, the malfunction diagnosis of the common wire can be carried out in accordance with the method as defined in claim 1, and advantageous effects similar to claim 1 can be obtained.

Further, as a concrete aspect of the above malfunction diagnosing means, preferably, as set forth in a presence embodiment (6), the malfunction diagnosing means is arranged to determine the presence or absence of occurrence of a malfunction in the common wire, based on the presence or absence of oscillations in the terminal voltage.

If the malfunction diagnosing means constructed in this way is used, the diagnosis of a malfunction in common wire can be carried out with satisfactory accuracy in accordance with the method as set forth in (2) above, and advantageous effects similar to those of (2) above can be obtained.

In order to measure a state of variations in terminal voltage at one connecting point excluding connecting points to which a common wire is connected, and its oscillated state and carry out a malfunction diagnosis, the malfunction diagnosing means may be configured so as to measure the frequency of the terminal voltage and determine the presence or absence of a malfunction, based on the measured frequency. As defined in a preferred embodiment (7), however, the malfunction diagnosing means may be constituted so as to have count means for accumulating a detected count one by one when the terminal voltage exceeds a preset threshold value and subsequently falls below the threshold value, or accumulating a detected count one by one when the terminal voltage falls below the threshold value and subsequently exceeds the threshold value, and determining means for determining whether the accumulated number of the detected counts has reached a predetermined value within a predetermined time and determining that a malfunction has occurred when the accumulated number of the detected counts has reached the predetermined value.

If the malfunction diagnosing means constructed in this way is taken, then the diagnosis of a malfunction in common wire can be carried out in accordance with the method as defined in (3) above, and advantageous effects similar to those of (3) aboved can be obtained.

In order to measure a state of variations in terminal voltage and its oscillated state at one connecting point excluding connecting points to which a common wire is connected, and carry out a malfunction diagnosis, the malfunction diagnosing means as defined in a preferred embodiment (8), may be constituted so as to include count means for accumulating a detected count one by one when the terminal voltage exceeds a preset first threshold value and subsequently falls below a second threshold value larger than the first threshold value, or accumulating a detected count one by one when the terminal voltage falls below the second threshold value and subsequently exceeds the first threshold value, and determining means for determining whether the accumulated number of the detected counts has reached a predetermined value within a predetermined time and determining that a malfunction has occurred when the accumulated number of the detected counts has reached the predetermined value.

If the malfunction diagnosing means constructed in this way is taken, then the diagnosis of a malfunction in common wire can be carried out, and advantageous effects similar to those of (4) above can be obtained.

EXPLANATIONS OF REFERENCE NUMERALS

Figure 1:
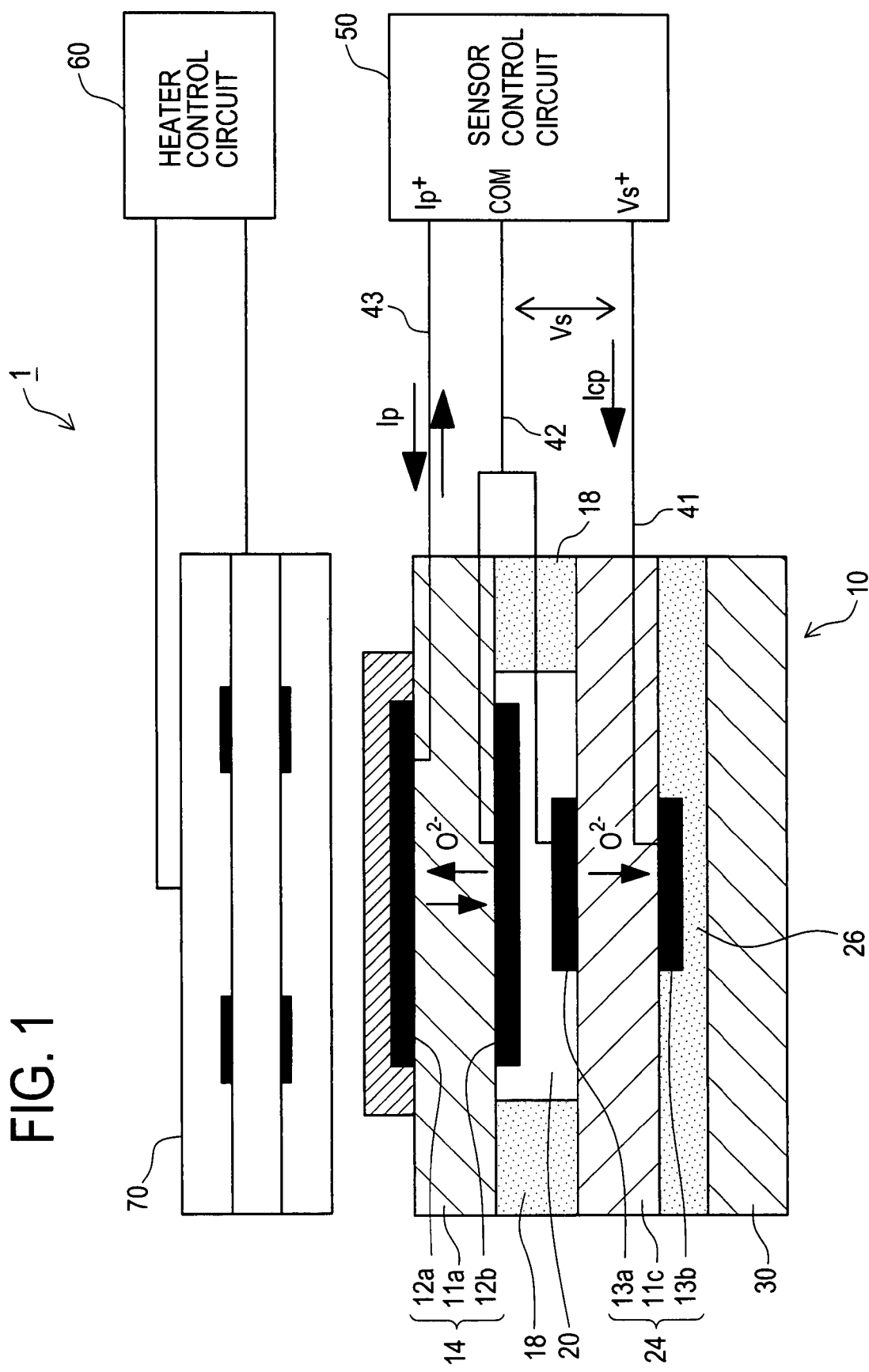
FIG. 1 is a configuration diagram schematically showing a gas concentration detecting unit 1.

1 Gas concentration detecting unit
10 Sensor element
11a First solid electrolytic layer
11c Second solid electrolytic layer
12a, 12b, 13a, 13b Porous electrode
14 Oxygen pump cell
20 Measurement chamber
24 Oxygen concentration detection cell
32 Op amplifier
42 Common wire
47 Detection resistor
50 Sensor control circuit
52 Sensor drive circuit
53 Malfunction detection circuit
54 Arithmetic processor
56 PID control circuit
61 Comparator
70 Ceramic heater

BEST MODE FOR CARRYING OUT THE INVENTION

A gas concentration detecting unit 1 equipped with a full-region air-fuel ratio sensor (hereinafter also simply referred to as a "UEGO sensor") and a sensor control circuit for driving and controlling the sensor will hereinafter be described as a preferred embodiment of the present invention, with reference to the accompanying drawings. Incidentally, the gas concentration detecting unit 1 according to the present embodiment is arranged to detect the concentration of oxygen contained in exhaust gas emitted from an internal combustion engine.

FIG. 1 is a schematic diagram illustrating the configuration of the gas concentration detecting unit 1. As shown in FIG. 1, the gas concentration detecting unit 1 comprises a sensor element 10 that constitutes the UEGO sensor, a sensor control circuit 50 which is electrically connected to the sensor element 10 to drive and control the sensor element 10, a ceramic heater 70 for heating the sensor element 10 to an operating temperature, and a heater control circuit 60 electrically connected to the ceramic heater 70 and adapted to drive and control the heater 70.

As shown in FIG. 1, the sensor element 10 includes an oxygen pump cell 14 in which porous electrodes 12a and 12b are placed on both surfaces (front and back surfaces) of a first solid electrolytic layer 11a, an oxygen concentration detection cell 24 in which porous electrodes 13a and 13b are placed on both surfaces (front and back surfaces) of a second solid electrolytic layer 11c, a measurement chamber 20 provided between the oxygen pump cell 14 and the oxygen concentration detection cell 24 and corresponding to a hollow space into which gas to be measured (exhaust gas in the present embodiment) is introduced, a diffusion porous layer 18 provided in a path for introducing the measured gas into the measurement chamber 20, and a shielding layer 30 laminated on the porous electrode 13b side of the oxygen concentration detection cell 24 with adhesive paste interposed therebetween and for forming an oxygen reference chamber 26 for storing oxygen between the oxygen concentration detection cell 24 and the oxygen reference chamber 26.

Incidentally, the porous electrode 12b of the oxygen pump cell 14 and the porous electrode 13b of the oxygen concentration detection cell 24 are located so as to face the measurement chamber 20. The first solid electrolytic layer 11a, the second solid electrolytic layer 11c and the shielding layer 30 are formed principally of partially stabilized zirconia made soluble or merged with yttria as a stabilizer. The porous electrodes 12a, 12b, 13a and 13b are formed principally of platinum. Further, the measurement chamber 20 is configured by forming, in a hollow manner, part of an insulating layer (not shown) formed principally of alumina, which is disposed between the oxygen pump cell 14 and the oxygen concentration detection cell 24. Further, the insulating layer is partly cut away such that its hollow portion and outer space communicate with each other, and a porous diffusion porous layer 18 formed principally of alumina is provided at its corresponding cut-away portion.

The ceramic heater 70 is of a plate form and placed opposite to the oxygen pump cell 24. And the ceramic heater 70 is provided therein with a heating resistance body 72. The temperature of the sensor element 10 is controlled by power supplied from the heater control circuit 60 so as to reach an arbitrary temperature between 550° C. and 900° C. corresponding to gas-concentration measurable active temperatures.

Figure 2:
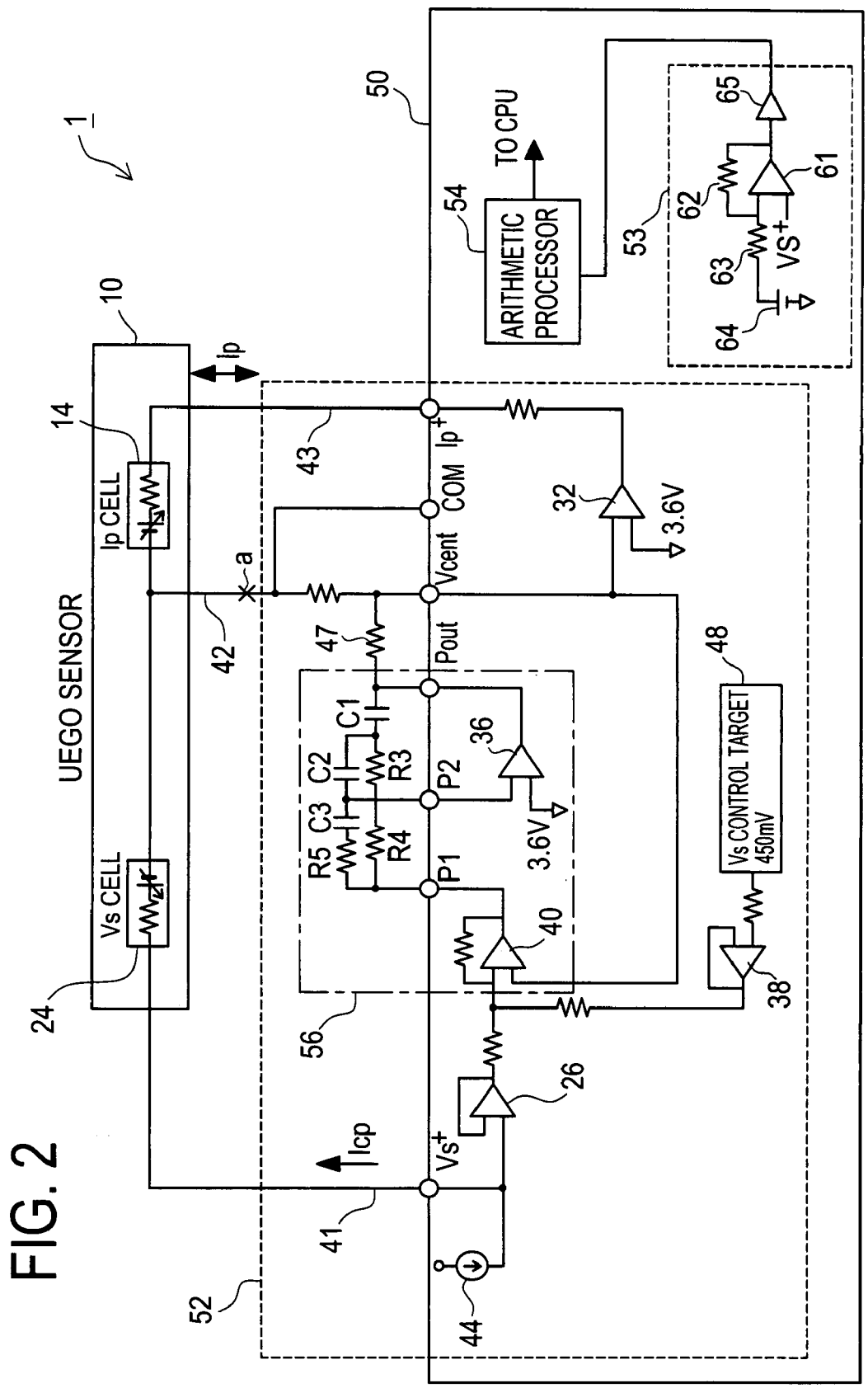
FIG. 2 is a circuit diagram showing the outline of a sensor control circuit 50 of the gas concentration detecting unit 1.

A configuration and operation of the sensor control circuit 50 will next be explained referring to FIG. 2. FIG. 2 is a circuit diagram showing the outline of the sensor control circuit 50.

As shown in FIG. 2, the sensor control circuit 50 has a sensor drive circuit 52 that drives and controls the oxygen pump cell 14 and the oxygen concentration detection cell 24 which constitute the sensor element 10. Further, the sensor control circuit 50 has a malfunction detection circuit 53 which receives a voltage at a Vs+ terminal corresponding to a connecting point between the porous electrode 13b of the oxygen concentration detection cell 24 and the sensor drive circuit 52 and which outputs a low level signal when it exceeds a predetermined first threshold voltage (4.2V) and outputs a low level signal when it is below a second threshold value (3.6V) smaller than the first threshold value, an arithmetic processor 54 which counts the number of times that the high level signal is outputted from the malfunction detection circuit 53, and determines whether the number of times has reached a predetermined number of times (32 times in the present embodiment) within a predetermined time period, etc. Incidentally, the sensor control circuit 50 having the sensor drive circuit 52, malfunction detection circuit 53 and arithmetic processor 54 is realized by an application specific integrated circuit (ASIC), for example.

The sensor drive circuit 52 principally comprises an operational (Op) amplifier 32 which allows a positive or negative pump current Ip to flow into the oxygen pump cell 14 such that the potential at a Vcent terminal to be described later is held constant; a PID control circuit 56 for improving a control characteristic of the pump current Ip (in other words, controlling the magnitude of the pump current Ip supplied to the oxygen pump cell 14); a constant current source 44 for allowing a small current Icp to pass through the oxygen concentration detection cell 24 to keep an oxygen concentration (in other words, oxygen concentration of the oxygen reference chamber 26) of the porous electrode 13b of the oxygen concentration detection cell constant; a constant voltage source 48 for supplying a control target voltage for the pump current Ip; a Vs+ terminal, a COM terminal, an Ip+ terminal and the Vcent terminal for connecting the sensor drive circuit 52 and the sensor element 10; a P1 terminal, a P2 terminal and a Pout terminal for externally providing circuit elements used to determine the characteristic of the PID control circuit 56; and a detection resistor 47 having one end connected to the Vcent terminal and the other end connected to the Pout terminal and used for converting the pump current Ip flowing through the oxygen pump cell 14 into voltage form.

In the oxygen pump cell 14, the porous electrode (electrode located on the side unfacing the measurement chamber 20) 12a located on its outer side is connected to the Ip+ terminal by a wire 43, whereas the porous electrode (electrode located on the side facing the measurement chamber 20) 12b located on its inner side is connected to the COM terminal by a common wire 42. Incidentally, the porous electrode 12b is connected even to the Vcent terminal through the common wire 42 other than the COM terminal. In the oxygen concentration detection cell 24, the porous electrode (electrode located on the side unfacing the measurement chamber 20) 13b located on its outer side is connected to the Vs+ terminal by a wire 41, whereas the porous electrode (electrode located on the side facing the measurement chamber 20) 13a located on its inner side is connected to the COM terminal and Vcent terminal through the common wire 42. Thus, the porous electrode 12b and the porous electrode 13a are set identical in potential by the common wire 42.

The Op amplifier 32 has an inversion input terminal connected to the PID control circuit 56, a non-inversion input terminal to which a reference voltage 3.6V is applied, and an output terminal connected to the Ip+ terminal.

The PID control circuit 56 comprises Op amplifiers 36 and 40, and resistors R3 through R5 and capacitors C1 through C3 which are mounted or applied to the P1 and P2 terminals and determine the control characteristic of the PID control circuit 56. One end side of the PID control circuit 56 is connected to the Vs+ terminal through the Op amplifier 26, and hence an output voltage Vs of the oxygen concentration detection cell 24 is inputted to the PID control circuit 56. The other end side of the PID control circuit 56 is connected to the Pout terminal. The Pout terminal is connected to the Vcent terminal through the detection resistor 47 and finally connected to the inversion input terminal of the Op amplifier 32. The PID control circuit 56 functions to perform a PID arithmetic operation on the amount of deviation ΔVs between a control target voltage 450 mV and the output voltage Vs of the oxygen concentration detection cell 24. The amount of deviation ΔVs is fed back to the output terminal of the Op amplifier 32 through the detection resistor 47 to cause a pump current Ip to flow into the oxygen pump cell 14.

The constant voltage source 48 supplies the voltage (450 mV) corresponding to the control target for controlling the Ip current to the PID control circuit 56 through the Op amplifier 38.

In the sensor drive circuit 52 configured as above, the oxygen in the measurement chamber 20 is deficient when the measured gas (exhaust gas) is in a state on the fuel oversupply (rich) side, and the output voltage Vs of the oxygen concentration detection cell 24 becomes higher than 450 mV corresponding to the control target voltage. Therefore, the amount of deviation ΔVs between the control target voltage and the output voltage Vs is generated and PID-operated by the PID control circuit 56, followed by being fed back to the output terminal of the Op amplifier 32, thereby allowing the pump current Ip for pumping deficient oxygen to the measurement chamber 20 by the oxygen pump cell 14.

On the other hand, when the measured gas (exhaust gas) is in a state on the fuel supply deficiency (lean) side, the oxygen in the measurement chamber 20 becomes excessive and the output voltage Vs of the oxygen concentration detection cell 24 becomes lower than 450 mV corresponding to the control target voltage. Therefore, the amount of deviation ΔVs is fed back to the output terminal of the Op amplifier 32 in the same manner as described above to allow a pump current Ip for pumping out excessive oxygen from the measurement chamber 20 by the oxygen pump cell 14 to flow.

That is, in the sensor element 10, the pumping-in and pumping-out of oxygen to and from the measurement chamber 20 are performed using the oxygen pump cell 14 so that the output voltage (electromotive force) Vs of the oxygen concentration detection cell 24 becomes constant (450 mV) (in other words, the air-fuel ratio of the measurement chamber 20 assumes a theoretical air-fuel ratio). Since the value and direction of the pump current Ip flowing through the oxygen pump cell 14 changes depending upon an oxygen concentration in the measured gas, the oxygen concentration of the measured gas can be detected based on the pump current Ip.

Incidentally, the above sensor drive circuit 52 is configured in such a manner that the pump current Ip flowing through the oxygen pump cell 14 is converted into voltage form by the detection resistor 47, and the voltage applied across the detection resistor 47 (between the Vcent terminal and the Pout terminal specifically) is outputted to a central processing unit (hereinafter, simply referred to as a "CPU") of the engine via an unillustrated differential amplifier circuit as a concentration signal. Then, the concentration signal outputted from the differential amplifier circuit is read into the CPU, where an oxygen concentration (air fuel ratio) is determined based on the concentration signal. Finally, air-fuel ratio feedback control of the internal combustion engine is performed based on the oxygen concentration (air fuel ratio) detected as above by the CPU.

Then, a description will be made on a malfunction diagnosing method using the malfunction detection circuit 53 and the arithmetic processor 54 in the sensor control circuit 50.

Firstly, the malfunction detection circuit 53 is provided with a comparator 61, and the voltage at the Vs+ terminal (the connecting point between the porous electrode 13a of the oxygen concentration detection cell 24 and the sensor control circuit 50) is inputted to an inversion input terminal of the comparator 61. Resistors 62 and 63, and a voltage source 64 are suitably connected to the comparator 61 to constitute a known comparator with hysteresis. An output terminal of the comparator 61 is connected to the arithmetic processor 54 through a buffer 65. In the comparator with the hysteresis, the sizes of the resistors 62 and 63 and voltage source 64 are adjusted in advance so that a voltage of 4.2V is inputted to the non-inversion input terminal of the comparator 61 when a high level signal is outputted from the output terminal, and a voltage of 3.6V is inputted to the inversion input terminal when a low level signal is outputted from the output terminal.

When the voltage at the Vs+ terminal exceeds 4.2V, the malfunction detection circuit 53 outputs a low level signal to the arithmetic processor 54, based on the output signal of the comparator 61. Since the voltage of 3.6V is inputted to the non-inversion input terminal when the low signal is outputted from the comparator 61, the voltage at the Vs+ terminal exceeds 4.2V. When the voltage at the Vs+ terminal falls below 3.6V subsequently, a high level signal is outputted from the comparator 61 to the arithmetic processor 54.

The operation of the malfunction detection circuit 53 will be explained below in further detail.

Figure 3:
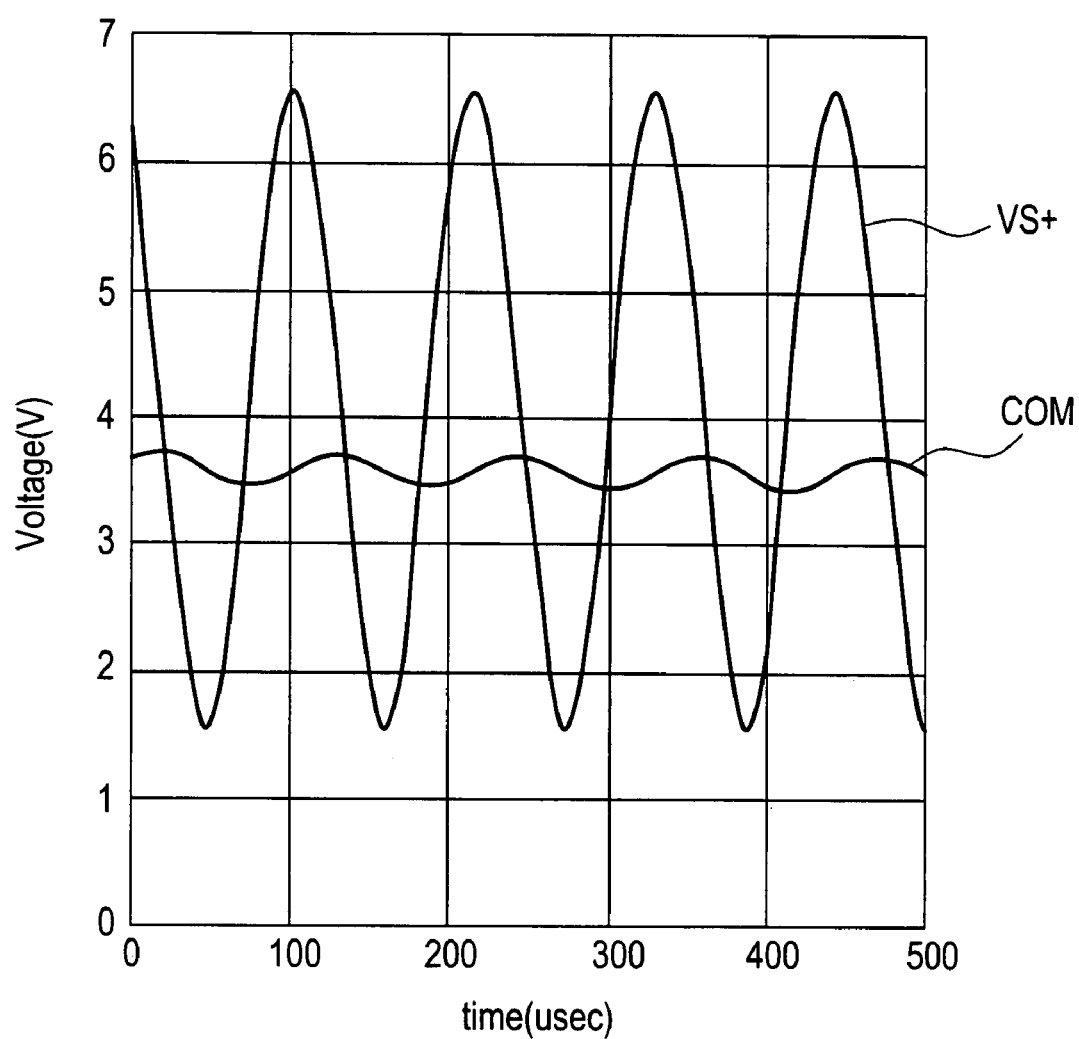
FIG. 3 illustrates voltage waveforms (voltage variations) at a Vs+ terminal and a COM terminal, which are recorded by a digital oscilloscope where a common wire 42 that connects a sensor element 10 and the sensor control circuit 50 (sensor drive circuit 52) in the gas concentration detecting unit shown in FIG. 2 is broken or disconnected.

As described above, the sensor control circuit 50 (more specifically, the sensor drive circuit 52) performs feedback control of the pump current Ip passed through the oxygen pump cell 24 with the output voltage Vs of the oxygen concentration detection cell 24 as a feedback voltage. When the common wire 42 connected to the Vcent terminal and the COM terminal breaks between the sensor element 10 and the sensor drive circuit 52 (at a point "a" in the figure) or a portion connected to the common wire 42 breaks inside the sensor element 10, the normal feedback control of the pump current Ip is not carried out, so that the sensor control circuit 50 produces oscillations between the Ip+ terminal and the VS+ terminal. The state of such oscillations is shown in FIG. 3. FIG. 3 shows a voltage waveform at the Vs+ terminal and a voltage waveform at the COM terminal, which are recorded by a digital oscilloscope where the common wire 42 that connects the sensor element 10 and the sensor drive circuit 52 is broken or disconnected at the point "a" shown in FIG. 2.

Thus, when the common wire 42 that connects the sensor element 10 and the sensor drive circuit 52 is broken, the voltage at the Vs+ terminal greatly varies with the oscillations. Described specifically, large variations in voltage occur in both a range in which its upper limit exceeds 6V and a range in which its lower limit falls below 2V, with 4.05V as the center. Incidentally, while the voltage waveform at the Vs+ terminal is shown in FIG. 3, the voltage at the Ip+ terminal also varies greatly with oscillations in a manner similar to the voltage waveform at the Vs+ terminal when the common wire 42 is broken.

When the common wire 42 that connects the sensor element 10 and the sensor drive circuit 52 actually breaks upon the operation of the sensor element 10, the variations in voltage are repeated in the range in which the upper limit exceeds 6V and the lower limit falls below 2V as mentioned above. Therefore, when the voltage at the Vs+ terminal exceeds 4.2V, the malfunction detection circuit 53 shown in FIG. 2 outputs a low level signal to the arithmetic processor 54, based on the output signal of the comparator 61, and outputs a high level signal from the comparator 61 to the arithmetic processor 54 when the voltage at the Vs+ terminal is below 3.6V subsequent to the above.

Figure 4:
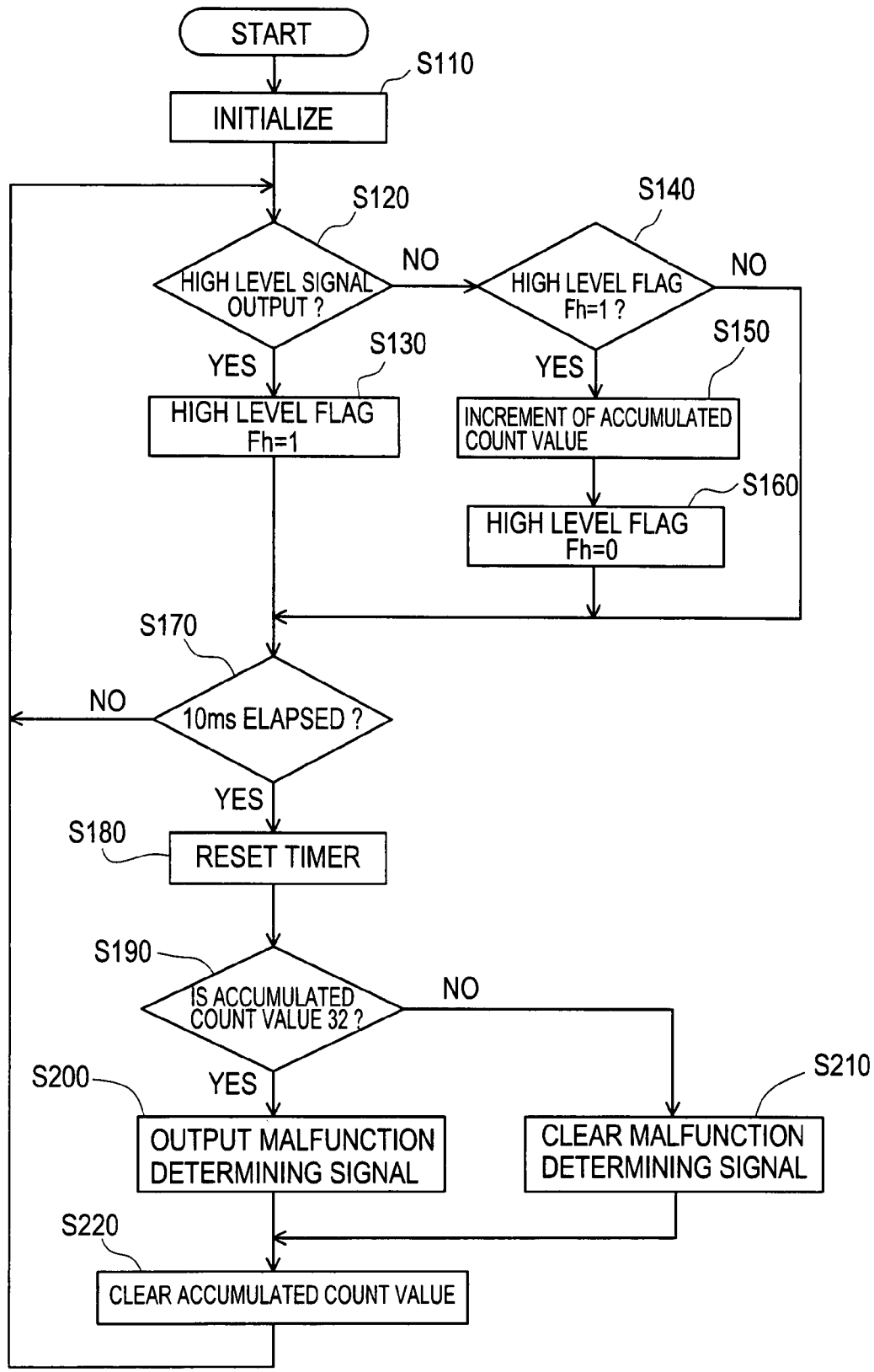
FIG. 4 is a flowchart showing the flow of a malfunction determining process executed by an arithmetic processor 54 that constitutes the sensor control circuit 50.

The contents of a malfunction determining process executed by the arithmetic processor 54 will next be explained. FIG. 4 is a flowchart showing the contents of the malfunction determining process. Incidentally, the arithmetic processor 54 starts an operation (malfunction determining process) in sync with at-key-on of the internal combustion engine.

When the malfunction determining process is first started, an initializing process is executed at S110 (where S indicates Step). Described specifically, a process for resetting an accumulated count value of a detection counter to 0, a process for clearing a malfunction determination or decision signal, a process for setting a high level flag Fh to Fh=0, a process for starting the measurement of a timer, etc. are executed.

At the next S120, it is determined whether the signal outputted from the malfunction detection circuit 53 is high in level. When it is found to be a high level (S120: Yes), then the malfunction determining process proceeds to S130, where the high level flag Fh is set to Fh=1 and thereafter the malfunction determining process proceeds to S170. When it is found not to be high in level at S120 (S120: No), then the malfunction determining process proceeds to S140.A5

At S140, it is determined whether the high level flag Fh is Fh=1. If the high level flag Fh=1 (S140: Yes), it is then determined that the signal outputted from the malfunction detection circuit 53 exceeds 4.2V and thereafter falls below 3.6V. Then, the malfunction determining process proceeds to S150, where the accumulated count value of the detection counter is incremented by 1. Next, the high level flag Fh is set to Fh=0 at S160, and the malfunction determining process proceeds to S170. On the other hand, when the high level flag Fh is found not to be Fh=1 at S140 (S140: No), the processes of S150 and S160 are skipped and the malfunction determining process proceeds to S170.

It is determined at S170 whether 10 ms has elapsed from the measurement made by the timer. If it is determined that 10 ms does not elapse (S170: No), then the malfunction determining process returns to S120 from which the processes subsequent to S120 referred to above are repeated. On the other hand, when it is determined that 10 ms has elapsed (S170: Yes), then the malfunction determining process proceeds to S180, where the measurement of the timer is reset and the present process is started again.

After the process of S180, it is determined at S190 whether the accumulated count value has reached 32 times. If the accumulated count value is found to have reached 32 times (S190: Yes), it is judged that the voltage at the Vs+ terminal has varied with oscillations because a malfunction (break, in concrete terms) has occurred in the common wire 42 that connects the sensor element 10 and the sensor drive circuit 52. Thereafter, the malfunction determining process proceeds to S200, where the arithmetic processor 54 outputs a malfunction determination signal to the CPU. When it is found at S190 that the accumulated count value does not reach 32 times (S190: No), it is determined that the common wire 42 is normal and the variation in the voltage at the Vs+ terminal is also stable. Then, the malfunction determining process proceeds to S210, where the output of the malfunction determination signal to the CPU is cleared.

After the process of S200 or S210, the malfunction determining process proceeds to S220, where the accumulated count value is cleared. When the process of S220 is completed, the malfunction determining process returns to S120 again and thereafter the processes of S120 to S220 are repeatedly executed.

Thus, the arithmetic processor 54 employed in the present embodiment repeatedly executes, based on the state of the variations in the voltage at the Vs+ terminal, a diagnosis (malfunction determining process) made as to whether the malfunction has occurred in the common wire 42 that connects the sensor element 10 and the sensor drive circuit 52.

Thus, in the sensor control circuit 50 employed in the gas concentration detecting unit 1 according to the present embodiment, the malfunction detection circuit 53 compares the voltage at the connecting point (Vs+ terminal) that connects the porous electrode 13b of the oxygen concentration detection cell 24 and the sensor drive circuit 52 with the two threshold values of 3.6V and 4.2V and determines whether the accumulation of the count (detected count) at which the terminal voltage exceeds 4.2V and falls below 3.6V subsequently, has reached 32 times within 10 ms, thereby detecting the malfunction of the common wire 42. By determining the oscillations produced between the Vs+ terminal and the Ip+ terminal, based on the state of the variations in the voltage at the Vs+ terminal upon the malfunction (break) of the common wire 42 in this way, whether the common wire 42 is being broken can be diagnosed easily and accurately.

In the present embodiment, the malfunction detection circuit 53 and the arithmetic processor 54 correspond to "malfunction diagnosing means" in the claims. The threshold value of 4.2V set in advance by the malfunction detection circuit 53 corresponds to "first threshold value", and the threshold value of 3.6V corresponds to "second threshold value". The processes of S120 to S160 in the malfunction determining process of the malfunction detection circuit 53 and the arithmetic processor 54 correspond to "count means" in the claims, and the processes of S170 to S210 in the malfunction determining process of the arithmetic processor 54 correspond to "determining means".

While the embodiment of the present invention has been explained above, the present invention is not limited to the above embodiment. It is needless to say that various forms can be taken as long as they belong to the technical scope of the present invention.

Although the malfunction detection circuit 53 has compared the voltage at the Vs+ terminal with the different threshold values (threshold values of 3.6V and 4.2V) in the present embodiment, the number of threshold values is set to only one and it may be compared with the voltage at the Vs+ terminal. It is however preferable to use the two different threshold values as the threshold values in terms of noise resistance as in the present embodiment.

In the present embodiment, the voltage at the Vs+ terminal is inputted to the malfunction detection circuit 53, where the variations in the voltage at the Vs+ terminal are detected. Since, however, the large variations in the voltage with the oscillations occur even in the voltage at the Ip+ terminal as described above where the break occurs in the common wire 42, the voltage at the Ip+ terminal is inputted to the malfunction detection circuit 53, where a malfunction (break) diagnosis of the common wire 42 may be performed according to the variations in the voltage at the Ip+ terminal.

Further, in the above embodiment, the detected count (accumulated count value) is accumulated one by one when the voltage at the Vs+ terminal exceeds the first threshold value (4.2V) set in advance and subsequently falls below the second threshold value (3.6V) under the malfunction determining process (flowchart shown in FIG. 4) of the arithmetic processor 54. However, the present process may be changed in such a manner that the detected count (accumulated count value) is accumulated one by one when the terminal voltage falls below the second threshold value (3.6V) and subsequently exceeds the first threshold value (4.2V). Alternatively, the detected count may be accumulated one by one when the voltage at the Vs+ terminal exceeds the first threshold value, whereas when the terminal voltage is below the second threshold value, the detected count is accumulated one by one and a decision as to whether the accumulated count value has reached a predetermined value within a predetermined time may be made.

The sensor element is not limited to one of the two-cell type of above form. The malfunction diagnosing method and malfunction diagnostic apparatus of the present invention can be applied even to a sensor element of three cells or more including at least an oxygen concentration detection cell and an oxygen pump cell. As the sensor element of three cells or more including the oxygen concentration detection cell and the oxygen pump cell, may be mentioned, an element intended for an NOx sensor and an element intended for an HC sensor, each of which forms the known configuration.

The invention claimed is:

1. A method for diagnosing a malfunction of a gas concentration detecting unit comprising:

a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein, and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the method comprising the step of:

diagnosing a malfunction of the common wire on the basis of a state of variations in terminal voltage at one or more of a plurality of connecting points for connecting the control circuit and the respective electrodes of the cells, wherein the connecting point is a connecting point other than a connecting point of the common wire, wherein the malfunction diagnosis of the common wire is executed in such a manner as to determine the presence or absence of occurrence of a malfunction in the common wire, based on the presence or absence of oscillations in the terminal voltage.

2. The method for diagnosing a malfunction of a gas concentration detecting unit according to claim 1, wherein the malfunction diagnosis of the common wire is executed in such a manner as to accumulate a detected count one by one when the terminal voltage exceeds a preset threshold value and subsequently falls below the threshold value, or accumulate a detected count one by one when the terminal voltage falls below the threshold value and subsequently exceeds the threshold value, and determine that a malfunction has occurred when the accumulated number of the detected counts has reached a predetermined value within a predetermined time.

3. The method for diagnosing a malfunction of a gas concentration detecting unit according to claim 1, wherein the malfunction diagnosis of the common wire is executed in such a manner as to accumulate a detected count one by one when the terminal voltage exceeds a preset first threshold value and subsequently falls below a second threshold value smaller than the first threshold value, or accumulate a detected count one by one when the terminal voltage falls below the second threshold value and subsequently exceeds the first threshold value, and determine that a malfunction has occurred when the accumulated number of the detected counts has reached a predetermined value within a predetermined time.

4. The method for diagnosing a malfunction of a gas concentration detecting unit according to claim 1, wherein the malfunction diagnosis of the common wire is executed in such a manner as to accumulate a detected count one by one when the terminal voltage exceeds a preset threshold value and subsequently falls below the threshold value, or accumulate a detected count one by one when the terminal voltage falls below the threshold value and subsequently exceeds the threshold value, and determine that a malfunction has occurred when the accumulated number of the detected counts has reached a predetermined value within a predetermined time.

5. The method for diagnosing a malfunction of a gas concentration detecting unit according to claim 1, wherein the malfunction diagnosis of the common wire is executed in such a manner as to accumulate a detected count one by one when the terminal voltage exceeds a preset first threshold value and subsequently falls below a second threshold value smaller than the first threshold value, or accumulate a detected count one by one when the terminal voltage falls below the second threshold value and subsequently exceeds the first threshold value, and determine that a malfunction has occurred when the accumulated number of the detected counts has reached a predetermined value within a predetermined time.

6. A malfunction diagnostic apparatus for a gas concentration detecting unit comprising:

a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein; and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the malfunction diagnostic apparatus comprising:

malfunction diagnosing means for diagnosing a malfunction of the common wire on the basis of a state of variations in terminal voltage at one or more of a plurality of connecting points for connecting the control circuit and the respective electrodes of the cells, wherein the connecting point is a connecting point other than a connecting point of the common wire, wherein the malfunction diagnosing means is arranged to determine the presence or absence of occurrence of a malfunction in the common wire, based on the presence or absence of oscillations in the terminal voltage.

7. The malfunction diagnostic apparatus for a gas concentration detecting unit, according to claim 6, wherein the malfunction diagnosing means includes, count means for accumulating a detected count one by one when the terminal voltage exceeds a preset threshold value and subsequently falls below the threshold value, or accumulating a detected count one by one when the terminal voltage falls below the threshold value and subsequently exceeds the threshold value, and determining means for determining whether the accumulated number of the detected counts has reached a predetermined value within a predetermined time and determining that a malfunction has occurred when the accumulated number of the detected counts has reached the predetermined value.

8. The malfunction diagnostic apparatus for a gas concentration detecting unit, according to claim 6, wherein the malfunction diagnosing means includes, count means for accumulating a detected count one by one when the terminal voltage exceeds a preset first threshold value and subsequently falls below a second threshold value smaller than the first threshold value, or accumulating a detected count one by one when the terminal voltage falls below the second threshold value and subsequently exceeds the first threshold value, and determining means for determining whether the accumulated number of the detected counts has reached a predetermined value within a predetermined time and determining that a malfunction has occurred when the accumulated number of the detected counts has reached the predetermined value.

9. The malfunction diagnostic apparatus for a gas concentration detecting unit, according to claim 6, wherein the malfunction diagnosing means includes, count means for accumulating a detected count one by one when the terminal voltage exceeds a preset threshold value and subsequently falls below the threshold value, or accumulating a detected count one by one when the terminal voltage falls below the threshold value and subsequently exceeds the threshold value, and determining means for determining whether the accumulated number of the detected counts has reached a predetermined value within a predetermined time and determining that a malfunction has occurred when the accumulated number of the detected counts has reached the predetermined value.

10. The malfunction diagnostic apparatus for a gas concentration detecting unit, according to claim 6, wherein the malfunction diagnosing means includes, count means for accumulating a detected count one by one when the terminal voltage exceeds a preset first threshold value and subsequently falls below a second threshold value smaller than the first threshold value, or accumulating a detected count one by one when the terminal voltage falls below the second threshold value and subsequently exceeds the first threshold value, and determining means for determining whether the accumulated number of the detected counts has reached a predetermined value within a predetermined time and determining that a malfunction has occurred when the accumulated number of the detected counts has reached the predetermined value.

11. A method for diagnosing a malfunction of a gas concentration detecting unit comprising:

a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein, and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the method comprising the step of:

diagnosing a malfunction of the common wire on the basis of a state of variations in a terminal voltage of connecting points for connecting the control circuit and the respective electrodes of the cells, measured at any single connecting point other than a connecting point of the common wire.

12. A malfunction diagnostic apparatus for a gas concentration detecting unit comprising:

a gas sensor including an oxygen pump cell including a first solid electrolytic layer and a pair of electrodes interposing the first solid electrolytic layer therebetween, an oxygen concentration detection cell including a second solid electrolytic layer and a pair of electrodes interposing the second solid electrolytic layer therebetween, and a measurement chamber in which a gas to be measured is introduced and one of the electrodes of each cell is placed therein; and a control circuit electrically connected to the respective electrodes of the cells, the control circuit controlling a current flowing through the oxygen pump cell so that a voltage outputted from the oxygen concentration detection cell will be a pre-set value, thereby controlling an oxygen concentration in the measurement chamber to a constant value, wherein the one electrodes of the respective cells, facing the measurement chamber, are connected to the control circuit via a common wire, the malfunction diagnostic apparatus comprising:

malfunction diagnosing means for diagnosing a malfunction of the common wire on the basis of a state of variations in a terminal voltage of connecting points for connecting the control circuit and the respective electrodes of the cells, measured at any single connecting point other than a connecting point of the common wire.

* * * * *